(12) United States Patent
Yang et al.

(10) Patent No.: US 12,292,494 B2
(45) Date of Patent: May 6, 2025

(54) METHODS AND SYSTEMS FOR SEGMENTING ORGANS IN IMAGES USING A CNN-BASED CORRECTION NETWORK

(71) Applicant: Washington University, St. Louis, MO (US)

(72) Inventors: Deshan Yang, St. Louis, MO (US); Yabo Fu, St. Louis, MO (US)

(73) Assignee: Washington University, St. Louis, MO (US)

( * ) Notice: Subject to any disclaimer, the term of this patent is extended or adjusted under 35 U.S.C. 154(b) by 1131 days.

(21) Appl. No.: 17/264,620

(22) PCT Filed: Jul. 30, 2019

(86) PCT No.: PCT/US2019/044118
§ 371 (c)(1),
(2) Date: Jan. 29, 2021

(87) PCT Pub. No.: WO2020/028352
PCT Pub. Date: Feb. 6, 2020

(65) Prior Publication Data
US 2021/0290096 A1 Sep. 23, 2021

Related U.S. Application Data

(60) Provisional application No. 62/850,225, filed on May 20, 2019, provisional application No. 62/712,619, filed on Jul. 31, 2018.

(51) Int. Cl.
*G01R 33/56* (2006.01)
*A61B 5/00* (2006.01)
(Continued)

(52) U.S. Cl.
CPC .......... *G01R 33/5608* (2013.01); *A61B 5/201* (2013.01); *A61B 5/4238* (2013.01);
(Continued)

(58) Field of Classification Search
None
See application file for complete search history.

(56) References Cited

U.S. PATENT DOCUMENTS 9,589,374 B1 3/2017 Gao et al.
9,965,863 B2 5/2018 Xu et al.
(Continued)

FOREIGN PATENT DOCUMENTS

CN 106204587 A 12/2016
WO WO 2018/052587 A1 3/2018

OTHER PUBLICATIONS

Abiodun Oi et al. (2018) State-of-the-art in artificial neural network applications: A survey. Heliyon. vol. 4, No. e00938, 41 pages.
(Continued)

*Primary Examiner* — Emily C Terrell
*Assistant Examiner* — Nathan J Bloom

(57) ABSTRACT

Among the various aspects of the present disclosure is the provision of methods and systems for segmenting images and expediting a contouring process for MRI-guided adaptive radiotherapy (MR-IGART) comprising applying a convolutional neural network (CNN), wherein the CNN accurately segments organs (e.g., the liver, kidneys, stomach, bowel, or duodenum) in 3D MR images.

9 Claims, 5 Drawing Sheets

(51) Int. Cl.
| | |
|---|---|
| *A61B 5/20* | (2006.01) |
| *G01R 33/48* | (2006.01) |
| *G06F 18/21* | (2023.01) |
| *G06F 18/214* | (2023.01) |
| *G06N 3/0455* | (2023.01) |
| *G06N 3/0895* | (2023.01) |
| *G06N 20/20* | (2019.01) |
| *G06T 7/12* | (2017.01) |
| *G06V 10/82* | (2022.01) |

(52) U.S. Cl.
CPC .......... *A61B 5/4244* (2013.01); *A61B 5/4255* (2013.01); *A61B 5/4836* (2013.01); *A61B 5/7267* (2013.01); *G01R 33/4808* (2013.01); *G06F 18/2148* (2023.01); *G06F 18/2185* (2023.01); *G06F 18/2193* (2023.01); *G06N 3/0455* (2023.01); *G06N 3/0895* (2023.01); *G06N 20/20* (2019.01); *G06T 7/12* (2017.01); *G06V 10/82* (2022.01); *G06T 2207/10088* (2013.01); *G06T 2207/20084* (2013.01); *G06T 2207/30056* (2013.01); *G06T 2207/30084* (2013.01); *G06T 2207/30092* (2013.01); *G06V 2201/031* (2022.01)

(56) References Cited

U.S. PATENT DOCUMENTS

| | | | |
|---|---|---|---|
| 10,147,187 B2 | 12/2018 | Wang et al. | |
| 10,223,610 B1* | 3/2019 | Akselrod-Ballin | G06T 7/174 |
| 2008/0304616 A1* | 12/2008 | Van Uitert, Jr. | G06T 7/12 600/407 |
| 2011/0212090 A1* | 9/2011 | Pedersen | A61K 39/464499 424/234.1 |
| 2017/0046616 A1* | 2/2017 | Socher | G06V 10/82 |
| 2018/0157939 A1* | 6/2018 | Butt | G06V 10/454 |
| 2018/0218502 A1 | 8/2018 | Golden et al. | |
| 2018/0276815 A1 | 9/2018 | Xu et al. | |
| 2018/0365888 A1* | 12/2018 | Satzoda | G05D 1/0251 |
| 2020/0019778 A1* | 1/2020 | Frei | A01B 59/042 |
| 2020/0193299 A1* | 6/2020 | Geva | G06N 3/088 |
| 2020/0279393 A1* | 9/2020 | Wolf | G06T 3/4046 |
| 2020/0380675 A1* | 12/2020 | Golden | G06T 7/143 |
| 2021/0177373 A1* | 6/2021 | Xie | A61B 8/463 |

OTHER PUBLICATIONS

Anderson D & McNeill G (1992) Artificial Neural Networks Technology. DACS State-of-the-Art Report, Kaman Sciences Corporation. 87 pages.
Arjovsky M et al. (2017) Wasserstein generative adversarial networks. Proceedings of the 34th International Conference on Machine Learning, PMLR, vol. 70, pp. 214-223.
Bengio Y et al. (1994) Learning long-term dependencies with gradient descent is difficult. IEEE Trans Neural Networks. vol. 5, No. 2, pp. 157-166.
Buda M et al. (2017) A systematic study of the class imbalance problem in convolutional neural networks. arXiv:1710.05381. 23 pages.
Chen L-C et al. (2016) Semantic image segmentation with deep convolutional nets and fully connected CRFs. ICLR 2015. arXiv:1412.7062v4. 14 pages.
Chen H et al. (2017) VoxResNet: deep voxelwise residual networks for brain segmentation from 3D Mr images. NeuroImage. vol. 170, pp. 446-455.
Chen L-C et al. (2018) DeepLab: semantic image segmentation with deep convolutional nets, atrous convolution, and fully connected CRFs. IEEE Trans Pattern Anal Mach Intell. vol. 40, No. 4, pp. 834-848.
Christ PF et al. (2016) Automatic liver and lesion segmentation in CT using cascaded fully convolutional neural networks and 3D conditional random fields. MICCAI 2016, Part II, LNCS 9901. pp. 415-423.
Christ PF et al. (2017) Automatic Liver and Tumor Segmentation of CT and MRI Volumes Using Cascaded Fully Convolutional Neural Networks. arXiv:1702.05970. 19 pages.
Çiçek Ö et al. (2016) 3D U-Net: learning dense volumetric segmentation from sparse annotation. MICCAI 2016, Part II, LNCS 9901. pp. 424-432.
Dai et al. (2017) Scan: Structure correcting adversarial network for organ segmentation in chest x-rays. DLMIA 2018/ML-CDS 2018, LNCS 11045, pp. 263-273.
Dolz J et al. (2017) 3D fully convolutional networks for subcortical segmentation in MRI: a large-scale study. NeuroImage. vol. 170, pp. 456-470.
Dosovitskiy A & Brox T (2016) Generating images with perceptual similarity metrics based on deep networks. 30th Conference on Neural Information Processing Systems (NIPS 2016). pp. 658-666.
Dou QP et al. (2017) 3D deeply supervised network for automated segmentation of volumetric medical images. Med Image Anal. vol. 41, pp. 40-54.
Fritscher K et al. (2016) Deep Neural networks for fast segmentation of 3D medical images. MICCAI 2016, Part II, LNCS 9901. pp. 158- 165.
Groza et al. (2018) Comparison of deep-learning based techniques for organ segmentation in abdominal CT images. $1^{st}$ Conference on Medical Imaging with Deep Learning (MIDL 2018). 3 pages.
Gulrajani I et al. (2017) Improved training of wasserstein GANs. Proceedings of the $31^{st}$ International Conference on Neural Information Processing Systems (NIPS 2017). pp. 5769-5779.
Hu et al. (2016) Automatic abdominal multi-organ segmentation using deep convolutional neural network and time-implicit level sets. Int J Comput Assist Radiol Surg, vol. 12, No. 3, pp. 399-411.
Hu P et al. (2016) Automatic 3D liver segmentation based on deep learning and globally optimized surface evolution. Phys Med Biol. vol. 61, pp. 8676-8698.
Huang G et al. (2017) Densely connected convolutional networks. 2017 IEEE Conference on Computer Vision and Pattern Recognition (CVPR). pp. 2261-2269.
Huttenlocher DP et al. (1993) Comparing images using the hausdorff distance. IEEE Trans Pattern Anal Mach Intell. vol. 15, No. 9, pp. 850-863.
International Search Report and Written Opinion for PCT/US2019/044118, mailed Nov. 1, 2019. 16 pages.
Ioffe S & Szegedy C (2015) Batch normalization: accelerating deep network training by reducing internal covariate shift. Proceedings of the $32^{nd}$ International Conference on Machine Learning. 9 pages.
Kamnitsas K et al. (2017) Efficient multi-scale 3D CNN with fully connected CRF for accurate brain lesion segmentation. Med Image Anal. vol. 36, pp. 61-78.
Krähenbühl P & Koltun V (2011) Efficient inference in fully connected CRFs with gaussian edge potentials. Advances in Neural Information Processing Systems 24 (NIPS 2011). 9 pages.
Lamb J et al. (2017) Online adaptive radiation therapy: implementation of a new process of care. Cureus. vol. 9, No. 8, e1618, 8 pages.
Lin G et al. (2016) Efficient piecewise training of deep structured models for semantic segmentation. 2016 IEEE Conference on Computer Vision and Pattern Recognition (CVPR). pp. 3194-3203.
Litjens G et al. (2017) A survey on deep learning in medical image analysis. Med Image Anal. vol. 42, pp. 60-88.
Lu F et al. (2016) Automatic 3D liver location and segmentation via convolutional neural network and graph cut. arXiv:1605.03012. 12 pages.
Mescheder LM et al. (2018) Which training methods for GANs do actually Converge? Proceedings of the $35^{th}$ International Conferences on Machine Learning. arXiv:1801.04406. 39 pages.
Milletari F et al. (2016) V-Net: fully convolutional neural networks for volumetric medical image segmentation. 2016 Fourth International Conference on 3D Vision (3DV), pp. 565-571.
Moeskops P et al. (2016) Automatic segmentation of MR brain images with a convolutional neural network. IEEE Trans Med Imaging. vol. 35, No. 5, pp. 1252-1262.

(56) References Cited

OTHER PUBLICATIONS

Moeskops P et al. (2016) Deep learning for multi-task medical image segmentation in multiple modalities. MICCAI 2016, Part II, LNCS 9901. pp. 478-486.

Mutic S & Dempsey JF (2014) The ViewRay system: magnetic resonance-guided and controlled radiotherapy. Semin Radiat Oncol. vol. 24, No. 3, pp. 196-199.

Noel CE et al. (2014) Segmentation precision of abdominal anatomy for MRI-based radiotherapy. Med Dosim. vol. 39, No. 3, pp. 212-217.

Ronneberger O et al. (2015) U-Net: convolutional networks for biomedical image segmentation. MICCAI 2015, Part III, LNCS 9351. pp. 234-241.

Roth et al. (2017) Hierarchical 3D fully convolutional networks for multi-organ segmentation. arXiv:1704.06382. 11 pages.

Roth K et al. (2017) Stabilizing training of generative adversarial networks through regularization. 31st Conference on Neural Information Processing Systems (NIPS 2017). 11 pages.

Shelhamer E et al. (2017) Fully convolutional networks for semantic segmentation. IEEE Trans Pattern Anal Mach Intell. vol. 39, No. 4, pp. 640-651.

Srivastava N et al. (2014) Dropout: a simple way to prevent neural networks from overfitting. J Mach Learn Res. vol. 15, pp. 1929-1958.

Wang et al. (2017) Interactive medical image segmentation using deep learning with image-specific fine tuning. IEEE Trans Med Imaging. vol. 37, No. 7. pp. 1562-1573.

Wooten Ho et al. (2015) Quality of intensity modulated radiation therapy treatment plans using a (6)(0)Co magnetic resonance image guidance radiation therapy system. Int J Radiat Oncol Biol Phys. vol. 92, No. 4, pp. 771-778.

Wooten Ho et al. (2015) Benchmark IMRT evaluation of a Co-60 MRI-guided radiation therapy system. Radiother Oncol. vol. 114, pp. 402-405.

Xing F et al. (2016) An automatic learning-based framework for robust nucleus segmentation. IEEE Trans Med Imaging. vol. 35, No. 2, pp. 550-566.

Xue Y et al. (2018) SegAN: adversarial network with multi-scale L 1 loss for medical image segmentation. Neuroinformatics. vol. 16, No. 3-4. pp. 383-392.

Yu L et al. (2017) Automatic 3D cardiovascular mr segmentation with densely-connected volumetric ConvNets. MICCAI 2017, Part II, LNCS 10434. pp. 287-295.

Zhang Z et al. (2018) Translating and segmenting multimodal medical vols. with cycle- and shape-consistency generative adversarial network. 2018 IEEE/CVF Conference on Computer Vision and Pattern Recognition. pp. 9242-9251.

Zhou X et al. (2017) Deep learning of the sectional appearances of 3D CT images for anatomical structure segmentation based on an FCN voting method. Med Phys. vol. 44, No. 10, pp. 5221-5233.

* cited by examiner (a)          (b)

ND SYSTEMS FOR
METHODS AND SYSTEMS FOR SEGMENTING ORGANS IN IMAGES USING A CNN-BASED CORRECTION NETWORK

CROSS-REFERENCE TO RELATED APPLICATIONS

This application claims the benefit of priority to PCT International Application No. PCT/US19/44118 filed on 30 Jul. 2019, which claims the benefit of U.S. Provisional Application Ser. No. 62/712,619 filed on 31 Jul. 2018 and U.S. Provisional Application Ser. No. 62/850,225 filed on 20 May 2019, which are incorporated herein by reference in their entireties.

STATEMENT REGARDING FEDERALLY SPONSORED RESEARCH OR DEVELOPMENT

This invention was made with government support under grant number R01-HS022888 awarded by Agency for Health Care Research and Quality (AHRQ). The government has certain rights in the invention.

MATERIAL INCORPORATED-BY-REFERENCE

Not Applicable.

FIELD OF THE INVENTION

The present disclosure generally relates to methods for MRI-guided adaptive radiotherapy (MR-IGART).

SUMMARY OF THE INVENTION

Among the various aspects of the present disclosure is the provision of a method of expediting a contouring process for MRI-guided adaptive radiotherapy (MR-IGART) comprising applying a convolutional neural network (CNN), wherein the CNN accurately segments organs (e.g., the liver, kidneys, stomach, bowel, duodenum) in 3D MR images.

An aspect of the present disclosure provides for a method of segmenting contours of one or more abdominal cavity organs. In some embodiments, the method comprises (i) providing an image dataset; (ii) applying a first convolutional neural network (sub-CNN1) to the image dataset, resulting in a label probability map of sub-CNN1 ($P_1$) (segmentation results); (iii) applying a correction network comprising a second convolutional neural network (sub-CNN2) and a third convolutional neural network (sub-CNN3) to $P_1$ comprising: (a) applying the second convolutional neural network (sub-CNN2) to the label probability map of sub-CNN1 ($P_1$), resulting in a label probability map of sub-CNN2 ($P_2$); (b) concatenating the image dataset, $P_1$, and $P_2$; or (c) applying the third convolutional neural network (sub-CNN3) to the image dataset, $P_1$, and $P_2$. In some embodiments, applying the first convolutional neural network and the correction network results in accurately segmented organs in images.

In some embodiments, the method comprises training sub-CNN1, sub-CNN2, and sub-CNN3. In some embodiments, training comprises: training each of sub-CNN1, sub-CNN2, and sub-CNN3 parameters using whole 3D images to incorporate anatomical contextual information; randomizing sub-CNN1, sub-CNN2, and sub-CNN3 parameters using a Gaussian distribution; calculating a cross entropy loss function using a softmax classifier for sub-CNN1, wherein sub-CNN2 and sub-CNN3 are constant; calculating a cross entropy loss function using a softmax classifier for sub-CNN2, wherein sub-CNN1 and sub-CNN3 are constant; or calculating a cross entropy loss function using a softmax classifier for sub-CNN3, wherein sub-CNN1 and sub-CNN2 are constant.

In some embodiments, one or more abdominal cavity organs are selected from gastrointestinal (GI) organs or organs at risk (OAR).

In some embodiments, the one or more abdominal cavity organs are selected from one or both kidneys, a liver, a stomach, a bowel, or a duodenum.

In some embodiments, the one or more abdominal cavity organs is an unstable organ selected from one or more of the group consisting of: a stomach, a bowel, or a duodenum.

In some embodiments, the label probability map of sub-CNN1 ($P_1$) (segmentation results) are refined through iterative error feedback comprising feeding erroneous labeling and the image dataset into the correction network, wherein the correction network iteratively corrects erroneous labels and improves segmentation accuracy.

In some embodiments, the image dataset is a MR image dataset or a CT image dataset.

In some embodiments, the correction network generates segmentations with possible organs shapes and locations; iteratively improves the $P_1$ (the segmentation results); is incorporated into the whole network and capable of being trained from end-to-end; or performs robustly and does not require careful parameter fine tuning.

In some embodiments, the correction network implicitly enforces anatomical constraints selected from the group consisting of: (i) shape of one or more organs or (ii) relative locations of multiple organs, wherein the relative locations among multiple organs comprises (a) kidney almost never appears anterior to a bowel and/or (b) stomach almost never touches a kidney.

In some embodiments, the correction network results in increased accuracy of segmentation results compared to densely connected conditional random field (CRF).

Another aspect of the present disclosure provides for a convolutional neural network (CNN)-based artificial neural network system implemented on a computer for organ segmentation by voxel-wise label prediction in images. In some embodiments, the system comprises: a first CNN sub-network (sub-CNN1); or a correction network comprising at least a second CNN sub-network (sub-CNN2) and a third CNN sub-network (sub-CNN3).

In some embodiments, the system comprises a 3D image dataset as input.

In some embodiments, the artificial neural network is trained using 3D images to incorporate anatomical contextual information.

In some embodiments, sub-CNN2 and sub-CNN3 learn to fix an erroneous classification of its previous network, sub-CNN1 and sub-CNN2, respectively; sub-CNN1 is configured to receive an input 3D image and generate predicted organ segmentation maps; or sub-CNN2 and sub-CNN3 enforce implicit anatomical constraints.

In some embodiments, sub-CNN1, sub-CNN2, and sub-CNN3 are trained, wherein training comprises: training each of sub-CNN1, sub-CNN2, and sub-CNN3 parameters using whole 3D images to incorporate anatomical contextual information; randomizing sub-CNN1, sub-CNN2, and sub-CNN3 parameters using a Gaussian distribution; calculating a cross entropy loss function using a softmax classifier for sub-CNN1, wherein sub-CNN2 and sub-CNN3 are constant; calculating a cross entropy loss function using a softmax classifier for sub-CNN2, wherein sub-CNN1 and sub-CNN3 are constant; or calculating a cross entropy loss function using a softmax classifier for sub-CNN3, wherein sub-CNN1 and sub-CNN2 are constant.

In some embodiments, the system comprises the use of an Adam optimizer with a constant learning rate.

In some embodiments, the organ segmentation is performed on unstable organs selected from the group consisting of a stomach, a bowel, or a duodenum, or a combination thereof.

In some embodiments, the system is used in conjunction with MRI-guided adaptive radiotherapy treatment systems, MRI-guided adaptive radiotherapy planning systems, or combination MRI-guided adaptive radiotherapy treatment and planning systems.

Another aspect of the present disclosure provides for an MRI-guided radiation treatment system comprising the use of the above-disclosed methods.

Another aspect of the present disclosure provides for an MRI-guided radiation treatment system comprising the CNN-based artificial neural network system described above.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

The present disclosure is based, at least in part, on the discovery that the presently disclosed convolutional neural network (CNN) (designed to accurately segment the liver, kidneys, stomach, bowel, and duodenum in 3D MR images) can expedite the contouring process for MRI-guided adaptive radiotherapy (MR-IGART). As shown herein, the disclosed method will be very useful in the MR image guided radiation therapy process for abdominal cancer treatments, especially for the online adaptive radiation therapy cases.

Here is described the automatic segmentation of the abdominal organs, particularly the gastrointestinal (GI) organs using a deep learning network comprising CNN and a correction network.

The presently disclosed CNN-based segmentation method accurately segments multiple organs including digestive organs in one single forward prediction. The CNN-based segmentation method comprises a correction network that implicitly enforces a certain level of anatomical constraints and iteratively improves the segmentation results. It is presently believed that this is the first time a CNN-based method was applied to segment both the stable organs such as the liver and kidneys and the unstable organs such as the stomach, bowel, and duodenum.

The disclosed system and methods can support online plan adaptation. Manual segmentation requires about 15 minutes, and disallows all possible automations (e.g., dose prediction, dose evaluation, plan re-optimization).

Figure 1:
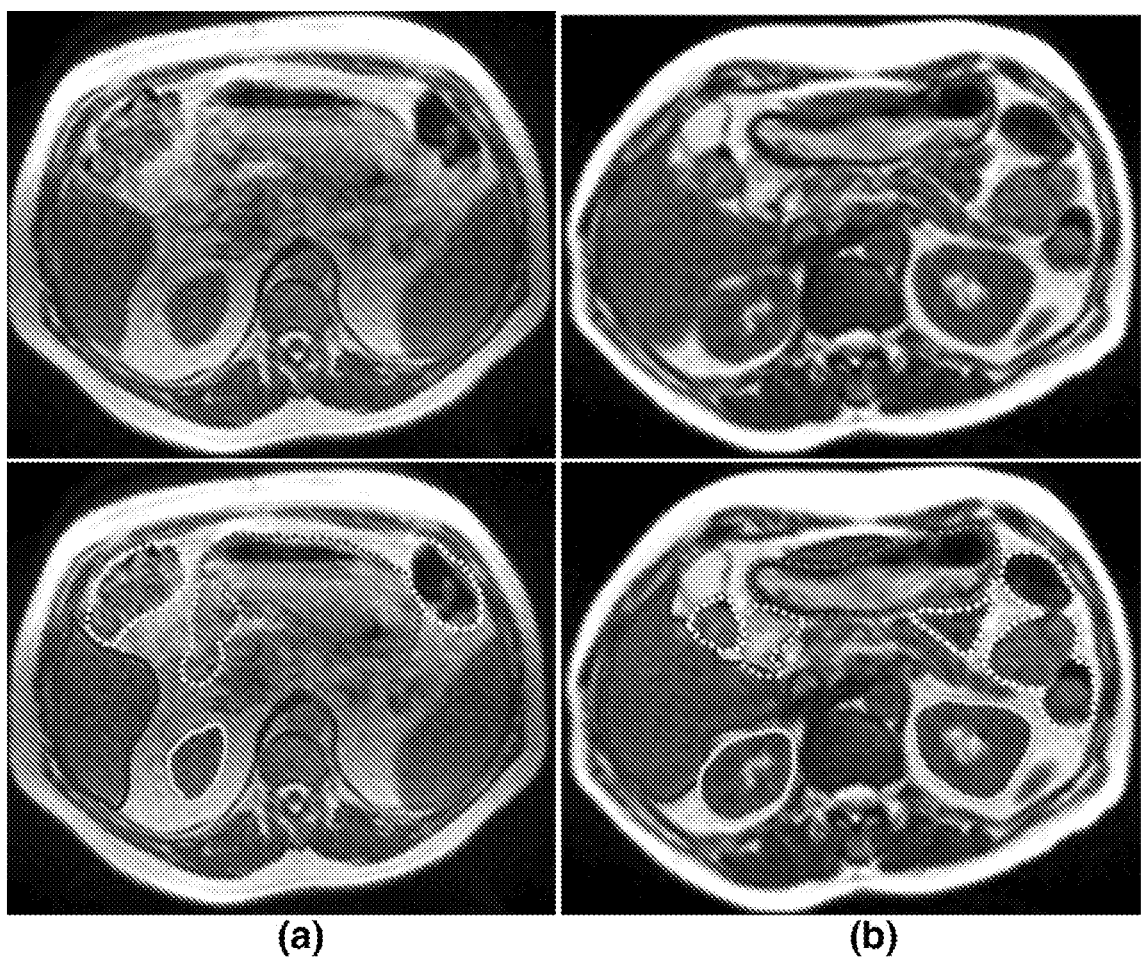
FIG. 1. Examples of manual contours in different datasets. Top row: original image, Bottom row: the manual contours. Stomach, bowel and duodenum are represented by dashed lines. Liver and kidneys are represented by solid lines.

The methods and systems described herein were shown to expedite the contouring process for MR-IGART and accurately contour multiple abdominal organs from a MR-guided radiation treatment system (e.g., a 3D Viewray MRI). As described herein (see e.g., Example 1), a dataset was prepared (see e.g., FIG. 1), a network was designed (see e.g., FIG. 2, FIG. 3), the parameters of the dataset and the model were trained, and the system was tested.

Convolutional Neural Network (Cnn) for Image Segmentation of Organs

Described herein is the use of a correction network to implicitly enforce certain level of anatomical constraints and generate segmentations with plausible organs shapes and locations. The correction network includes multiple sub-CNNs that implicitly learn the global context and rectify the spurious labeling from previous sub-CNNs. The global context can include where each and every organ is relatively located, respective to the whole abdomen and pelvis, and respective to other organs in the abdomen and pelvis. For example, the liver is always located to the right side of the abdomen, under the right liver, and spleen is always on the left side. Instead of predicting the labeling output in a single step (like conventional CNN), the correction network refines the segmentation results through iterative error feedback by feeding the erroneous labeling along with the original image into the correction network. Unlike the CRF which is an add-on post-processing step, the correction network can be effectively incorporated into the whole network and trained from end-to-end. Unlike the hard-to-train GAN or WGAN networks which need subtle parameters fine tuning for convergence, the correction network can perform robustly and does not require careful parameter fine tuning.

The correction network can comprise sub-CNNs, where sub-CNN can comprise a dense block, a batch normalization (BN), ReLU, a fully connected layer, and/or transpose convolution layers, or a suitable substitution thereof.

Medical image segmentation has been studied for decades but remains a challenging problem today. Since the invention of the convolutional neural network (CNN), there have been many attempts to utilize CNNs for various image segmentation tasks. Most of the early methods used a simple "sliding window" approach which has many drawbacks including huge overlap of image patches and repeated convolution for the same pixel. In 2015, Shelhamer et al. proposed a fully convolutional network for image segmentation. Instead of using "sliding window", transpose convolutional layers were applied to up-sample output images to achieve dense inference. In the same year, Ronneberger et al. proposed a novel architecture, called U-Net, which consists of equal numbers of down-sampling and up-sampling layers to segment cell structures. After the invention of U-Net, many CNN-based segmentation methods have been proposed and have achieved state-of-the-art performances in different medical image segmentation tasks. Cicek et al. extended the 2D U-Net to 3D and trained their CNN model using only sparse annotations. They achieved an average Dice coefficient of 0.863 on *Xenopus* kidney segmentation using semi-auto segmentation. Zhou et al. proposed a fully convolutional network with 3D major voting for 3D CT image segmentation of 19 types of targets in the human body. The network was trained using multiple 2D slices and then integrated for 3D classification by major voting. Lu et al. used a 3D CNN with 11 convolution layers to segment liver from CT images. The segmentation results of liver on CT were post-processed using the graph cut method. Hu et al. used a similar CNN architecture for liver segmentation. The results were refined using globally optimized surface evolution. V-Net was proposed by Milletari et al. to segment the prostate on MRI. V-Net used a different objective function that was based on Dice coefficients to overcome the class imbalance problem. Many CNN-based methods have been proposed to segment the human brain. Moeskops et al. used a multi-scale CNN method to segment 6 brain tissues from MRI. Kamnitsas et al. proposed a multi-pathway CNN network, called DeepMedic, to segment brain lesions. The results of the DeepMedic network were further refined using a Conditional Random Field (CRF) model. A 3D deeply supervised network was proposed by Dou et al. to segment liver and heart from 3D MR images. The network was deeply supervised in the sense that the loss function was calculated using outputs from multiple layers. Huang et al. proposed a densely connected convolutional network (DenseNet) and achieved state-of-the-art performance on natural image classification and recognition. DenseNet explored the idea of feature reuse which alleviated the gradient exploding/vanishing problem and made the network converge faster. Yu et al. proposed a DenseVoxNet which extended the DenseNet to cardiac segmentation on 3D MR images.

Up to now, most CNN-based segmentation methods have focused on the brain and liver because they are stable organs. Very few methods have been proposed to segment the digestive organs, due to the instability of the organs. As disclosed herein, the segmentation targets include both stable organs (liver and kidney) and unstable digestive organs (stomach, bowel, and duodenum) from 3D MR images. It is very challenging for the CNN to learn stable representative features for the digestive organs because the appearances, shapes, and sizes of these organs are highly unstable from day to day depending on different food intake and digestion process.

Aside from the intensity information, the shapes and locations of the target organs also provide important cues for accurate manual segmentation. CNN methods which are trained to represent high-level textural information could generate segmentations that tend to preserve the shapes of the target objects because pixels from the same objects often share substantial similar appearance textures. However, the CNN methods may generate suboptimal segmentation such as inaccurate delineation and noisy small spurious labeling due to the lack of necessary contextual constraints that encourage spatial smoothness and plausible shapes of the target objects. In the presently disclosed segmentation task, examples of the necessary anatomical constraints include the shape of each organ and the relative locations among multiple organs such as (a) kidney almost never appears anterior to the bowel, (b) stomach almost never touches kidney and so on.

CRF has been frequently applied as a post-processing step to improve the segmentation results. Densely connected CRF (DC-CRF) was proposed to explicitly model the global pairwise relationships of each pixel with every other pixel in the image. However, DC-CRF is extremely memory intensive and usually impractical for strict implementation especially for large 3D datasets. To alleviate the problem, Philipp Krahenbuhl et al. proposed to use combination of high-dimensional filters for efficient approximation of DC-CRF. Lin et al. built a deep structured model by only modeling the output labeling dependency within a small neighborhood region. However, these methods tend to work locally and do not effectively enforce the global dependencies due to the small filtering kernel sizes and the small neighborhood region. Moreover, it is challenging to find a global set of parameters for the CRF that can consistently improve the segmentation results for all classes in multi-class segmentation.

Generative Adversarial Networks (GAN) have also been applied to help CNN to predict plausible structural labeling by employing a discriminator which learns to discriminate between the CNN-predicted labels and the ground truth labels. One disadvantage of GAN is that it is very difficult to train and is very sensitive to hyperparameters. To facilitate easy training, Martin Arjovsky et al. proposed a Wasserstein GAN (WGAN) which uses Wasserstein distance as an improved differentiable metric during the training. However, Mescheder et al. showed that the WGAN method does not provide guaranteed convergence. It was attempted to employ both GAN and WGAN to solve the specific multi-organ segmentation task without success, which shows the difficulty to train a GAN.

Dataset

As described herein, a dataset can be prepared from any CT or MR image (e.g., for use in a MR-guided radiation treatment system). The dataset can include contours from gastrointestinal (GI) organs and organs at risk (OAR) (e.g., pancreas, liver, stomach, adrenal gland, and prostate). A dataset can be prepared by manually contouring the GI and OAR organs. The dataset can be a training dataset, a validation dataset, or a testing dataset. The dataset can be cropped, down-sampled, and padded (e.g., to a 128×128×64 size) to avoid memory overflow. For example, the datasets can be prepared using an amount of datasets sufficient to train the network. For example, the datasets can be prepared using about 120 MR-guided radiation treatment system (e.g., Viewray) patient datasets. The datasets can include GI and OARs, such as the pancreas, liver, stomach, adrenal gland, or prostate. Manually and carefully contoured liver, kidneys, stomach, duodenum, and bowel were used for the training, validation, and testing datasets (e.g., 100 training datasets, 10 validation datasets, and 10 testing datasets were utilized). The datasets can be cropped, down-sampled, and padded to, for example, 128×128×64 size.

Training

Training of the network can be performed by any training method currently known in the art (see e.g., Abiodun et al. State-of-the-art in artificial neural network applications: A survey Heliyon 4 (2018) e00938). For example, training of the network can be performed by piecewise training of sub-CNNs using an optimizer, such as an Adam optimizer with a constant learning rate between about 1e-4 and 0.4. A batch size of 1 or more can be used. At least about 100 epochs can be used.

Testing

Testing can be performed on MR datasets. Measuring the effects of the correction network was performed by comparing to CNN and CNN+CRF.

As described herein, DICE and Hausdorff distances were measured, segmentation results were compared, and improved contouring time analysis was demonstrated. Dice coefficients and Hausdorff distance (HD) were calculated to evaluate segmentation accuracy of the disclosed method. These calculated values showed that the present disclosure provides a more accurate method to segment organs than another method, conditional random field (CRF), where CRF is conventionally used only as a post-processing step. Results are described in Example 1. As described herein, the presently disclosed network can expedite the contouring process for MR-IGART.

MR-IGART

Shown herein are methods and systems to expedite the contouring process for MRI-guided adaptive radiotherapy (MR-IGART). As described herein, a convolutional neural network (CNN) was designed to accurately segment the liver, kidneys, stomach, bowel, and duodenum in 3D MR images.

As shown herein, the disclosed method can be used in the MR image guided radiation therapy process for abdominal cancer treatments, especially for the online adaptive radiation therapy cases.

As described herein, the MRldian (ViewRay Inc. Oakwood Village, OH, USA) radiation treatment system combines real-time MR image guidance and intensity modulated radiation therapy (IMRT) technologies to allow soft tissue visualization and accurate tumor targeting. In addition, MRldian has the capability of online MR image-guided adaptive radiotherapy (MR-IGART). With MR-IGART, treatment plans can be adapted to the daily patient anatomy just prior to a fraction to maximize target coverage while minimizing the toxicities to the surrounding organs-at-risk (OAR).

Contouring Organs

As described herein, accurate contouring of critical OARs is one of the keys to MR-IGART. Contouring uncertainties can translate into undesired dose distributions on actual anatomy, however, manual OAR contouring is a time-consuming process which is subject to inter-observer variation. The time required by the contouring process is a principal bottleneck for treatment plan adaptation. Reported by Lamb et al. after studying 80 online MR-IGART cases, the median time of the adaptive process prior to beam delivery was 54 min, with the re-contouring process requiring up to 22 min. Although the ViewRay treatment planning and delivery system can automatically propagate planning contours based on deformable image registration (DIR), Lamb et al. found that it was preferable to manually re-contour the OARs from scratch due to unsatisfactory automatic contour propagation results. The slow manual re-contouring process can limit the patient treatment throughput, decrease patient comfort, increase the effect of intra-fraction organ motion and decrease the effectiveness of online plan adaptation. Automatic and accurate OAR segmentation methods, as described herein, can greatly benefit MR-IGART.

The methods and algorithms of the invention may be enclosed in a controller or processor. Furthermore, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: A Novel MRI Segmentation Method Using CNN Based Correction Network for MRI-Guided Adaptive Radiotherapy The following example describes methods to expedite the contouring process for MRI-guided adaptive radiotherapy (MR-IGART). A convolutional neural network (CNN) was designed to accurately segment the liver, kidneys, stomach, bowel, and duodenum in 3D MR images.

The purpose of this study was to expedite the contouring process for MRI-guided adaptive radiotherapy (MR-IGART) by developing a convolutional neural network (CNN) deep-learning (DL) model that can accurately segment the liver, kidneys, stomach, bowel, and duodenum in 3D MR images.

Images and structure contours for 120 patients were collected retrospectively. Treatment sites included pancreas, liver, stomach, adrenal gland, and prostate. The disclosed DL model contains a voxel-wise label prediction CNN and a correction network which consists of two sub-networks. The prediction CNN and sub-networks in the correction network each includes a dense block which consists of twelve densely connected convolutional layers. The correction network was designed to improve the voxel-wise labeling accuracy of a CNN by learning and enforcing implicit anatomical constraints in the segmentation process. Its sub-networks learn to fix the erroneous classification of its previous network by taking as input both the original images and the softmax probability maps generated from its previous sub-network. The parameters of each sub-network were trained independently using piecewise training. The model was trained on 100 datasets, validated on 10 datasets and tested on the remaining 10 datasets. Dice coefficient and Hausdorff distance (HD) were calculated to evaluate the segmentation accuracy.

The disclosed DL model was able to segment the organs with good accuracy. The correction network outperformed the conditional random field (CRF), a most comparable method that is usually applied as a post-processing step. For the 10 testing patients, the average Dice coefficients were 95.3±0.73, 93.1±2.22, 85.0±3.75, 86.6±2.69, and 65.5±8.90 for liver, kidneys, stomach, bowel, and duodenum, respectively. The mean Hausdorff Distance (HD) were 5.41±2.34, 6.23±4.59, 6.88±4.89, 5.90±4.05, and 7.99±6.84 mm, respectively. Manual contouring, as to correct the automatic segmentation results, was four times as fast as manual contouring from scratch.

The disclosed method can automatically segment the liver, kidneys, stomach, bowel, and duodenum in 3D MR images with good accuracy. It is useful to expedite the manual contouring for MR-IGART.

Material and Methods

Datasets

MRI datasets of 120 ViewRay patients were retrospectively collected with IRB approval. Treatment sites of the 120 patients include pancreas, liver, stomach, adrenal gland, and prostate. All patient images were originally acquired for daily image guidance or MR-IGART with a balanced steady-state free precession pulse sequence (TrueFISP). In-plane resolution was 1.5×1.5 mm$^2$ and slice thickness was 3 mm.

Liver, both kidneys, stomach, duodenum, and bowel were manually contoured. Accurate contouring is essential for the training of a high-quality network. A special in-house software was developed with sophisticated functions to support accurate delineation and contour refinement. The contours were sequentially checked and refined by multiple trained professionals to make sure the final contours were of high quality. The manual contouring process was very time-consuming because of several reasons. First, the datasets include 120 cases with an average image size of 256×256× 64 voxels. Second, digestive organs especially duodenum and bowel are difficult to contour manually. The appearances of bowel and duodenum are often blurred because of the abdominal motion. Image quality is significantly lower than diagnostic MRIs due to the low MRI field strength (0.3 T) and the quick (17 or 25 s) 3D MRI scan sequences. Bowel and duodenum are usually very difficult to track. Duodenum sometimes does not show clear boundaries on the image because patients often cannot hold breath during the quick MRI scans. In the case shown in FIG. 1(a), the duodenum was essentially invisible, had to be manually contoured relying on anatomical knowledge. Manual contouring of such cases was very subjective and time-consuming. Contouring of bowel was also a very time-consuming procedure which usually required repeated slices navigation back and forth to follow the tubular structure in the axial view (the view in the highest image resolution). In the example shown in FIG. 1(b), the target organs are very close to each other. This makes it challenging to accurately delineate the organ boundaries. On average, it took around 2 h to contour each dataset and totally ~240 h to contour all the 120 datasets.

In preprocessing, all MRIs were cropped to keep only the relevant region covering the organs of interest. Instead of patch-based training, the network was trained on the whole images to preserve the global anatomical constraints such as the relative locations among the target organs. However, training on the whole images is very memory intensive. Therefore, the images were resampled and zero-padded to 128×128×64 pixels to avoid GPU memory overflow.

Network Architecture

Figure 2:
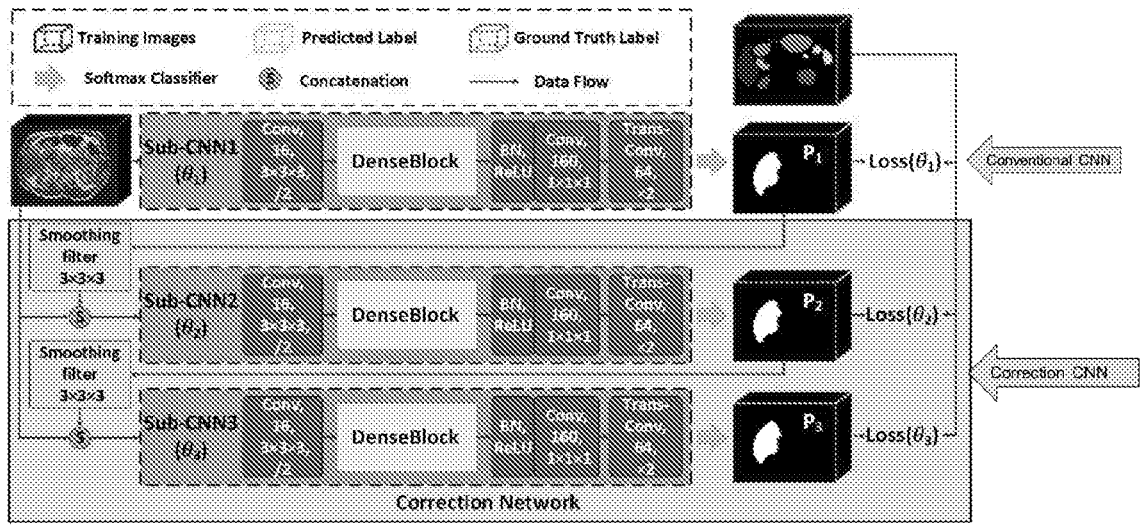
FIG. 2. The architecture of the disclosed network.
Figure 3:
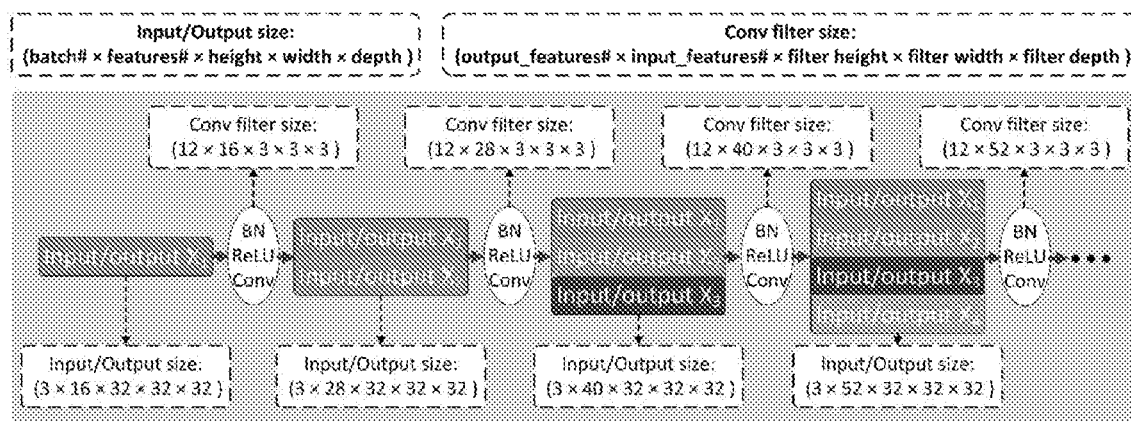
FIG. 3. The architecture of a dense block. The first four convolutional layers of the dense block in FIG. 2 are illustrated. Input/Output image sizes and convolutional filter sizes are shown in dashed boxes. $X_1$, $X_2$, $X_3$, $X_4$ are concatenated in the next layer to achieve dense connectivity.

The architecture of the disclosed network is shown in FIG. 2. The network consists of three sub-CNN networks represented by the gray-dashed boxes. The sub-CNN2 and sub-CNN3 are the correction network that is used to improve the segmentation results of sub-CNN1 ($P_1$). The label probability maps $P_1$ and $P_2$ were smoothed using a mean filtering kernel of 3×3×3 size to encourage spatial continuity and smoothness. The original images and the smoothed label probability maps from a sub-CNN were concatenated and fed to the next sub-CNN as input. Each sub-CNN contains a dense block, a batch normalization (BN), ReLU, a fully connected layer and transpose convolution layers. The dense block is essentially 12 densely connected convolutional layers as shown in FIG. 3. The dense block design was chosen because it was efficient in high-level feature learning and could potentially alleviate the problem of gradient exploding/vanishing by encouraging information propagation from previous layers. Before the dense block, a convolution stride of two was designed to halve the feature map size while keeping a large reception field. The transpose convolution layers were used to up-sample the feature maps to the size of the original input images. The batch normalization layers (BN) before each convolution layer were designed to reduce internal covariate shift of the input data to each layer. Each sub-CNN has its own loss function denoted by Loss (ei) in FIG. 2. To alleviate the problem of potential overfitting, a dropout layer was appended to each convolutional layer with an empirical dropout rate of 0.2.

Training Configuration

The disclosed network was implemented using Tensorflow. The network was trained from end-to-end using piece-wise training as the parameters of the sub-CNN were trained by minimizing its corresponding loss function while keeping the parameters of other sub-CNNs constants. Softmax cross-entropy was used in the loss calculations. The training parameters were initialized randomly using a Gaussian distribution (mean=0, SD=0.01). The network was trained using Adam optimizer with a constant learning rate of 1e-4. The learning process was assessed using the 10 validation datasets at every 500 iterations. The training process was stopped if the mean DICE did not improve for five consecutive validations, for example, 2500 iterations. The network presented in herein was converged after 300 epochs. A GeForce GTX 1080 Ti GPU with 11 GB RAM and 3584 CUDA cores was used for training.

Results

Figure 4:
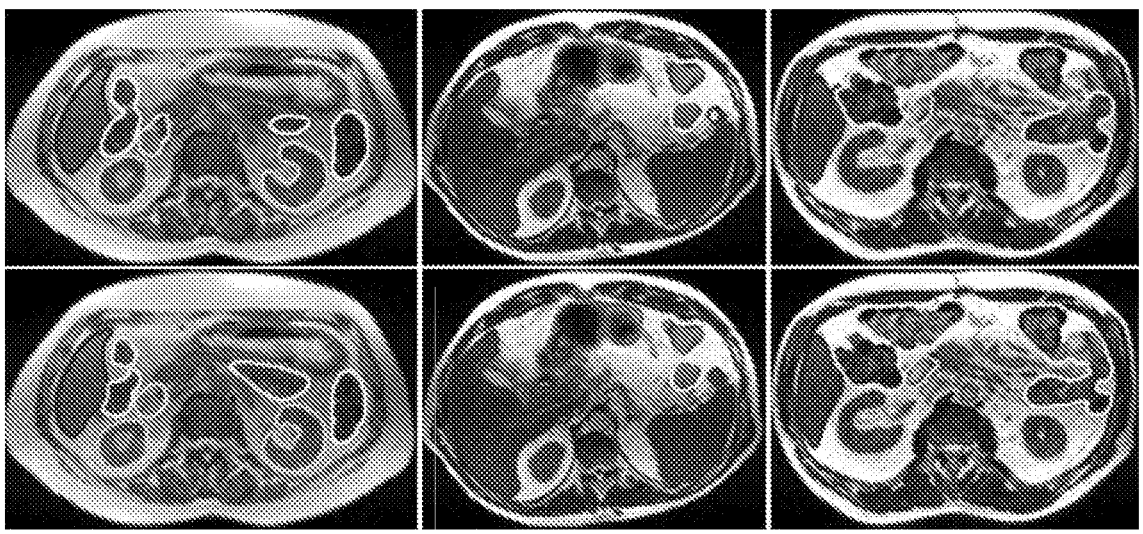
FIG. 4. Top row: segmentation results, Bottom row: the ground truth.
Figure 5:
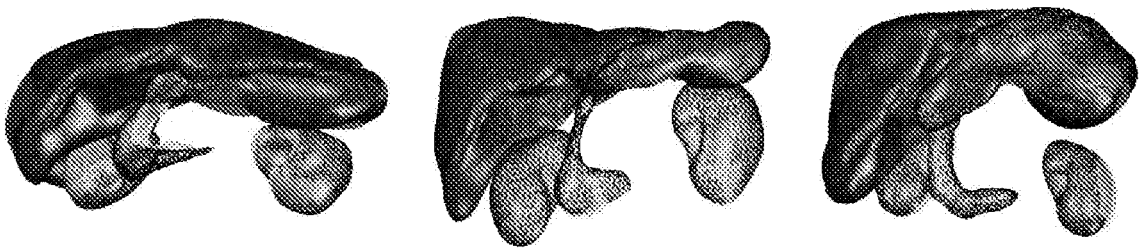
FIG. 5. 3D surfaces comparison between segmentation results and the ground truth. The ground truths were represented by meshes. The segmentation results were represented by surfaces.

The segmentation results of the disclosed method are demonstrated in FIG. 4 in 2D on selected slices of three datasets. Despite large variations in appearances, shapes, and sizes of stomach and bowel, the disclosed method was able to segment these organs with high accuracy. To compare the results in 3D, the surfaces of the segmentation results are overlaid on the ground truth in FIG. 5. To avoid occlusion, bowels are not displayed. Ground truths are represented by black meshes while segmentation results are represented by surfaces in color. The surfaces of the segmented organs are in good agreement with the ground truth. The results of duodenum are generally not as good as that of the liver, kidney, and stomach. During the manual contouring, it was found to be most challenging to contour the small duodenum because of its small sizes and blurred image contrasts.

Spurious Labeling Correction

The performance of the disclosed method was evaluated on the 10 testing datasets. For comparison purpose, the segmentation results of sub-CNN1 were post-processed using a DC-CRF and were compared with the outputs of the correction network. Philipp Krahenbuhl et al., showed that the pairwise terms of DC-CRF can be approximated using high-dimensional filtering. The filtering kernels were defined as:

$$k(i,j) = w_1 \exp\left(-\frac{|p_i - p_j|^2}{2\theta_\alpha^2} - \frac{|I_i - I_j|^2}{2\theta_\beta^2}\right) + w_2 \exp\left(-\frac{|p_i - p_j|^2}{2\theta_\gamma^2}\right)$$

The kernel is essentially a weighted combination of bilateral filtering and Gaussian filtering. The first exponential term weighted by $w_1$ is the bilateral kernel, which encourages nearby similar pixels be assigned the same label. The second exponential term weighted by $w_2$ is the Gaussian kernel which encourages local spatial smoothness. For fast inference, $\theta_x$ and $\theta_y$ was set to be 3 pixels. Optimal $\theta_\beta$ was set using grid search. One advantage of the bilateral filtering is that it could preserve the sharpness of the labels by only averaging over voxels of similar image intensity. On the contrary, the Gaussian filtering, if applied multiple times, could generate over-smoothed label maps. Therefore, the bilateral filtering was applied five times and the Gaussian filter only once in the implementation.

Figure 6:
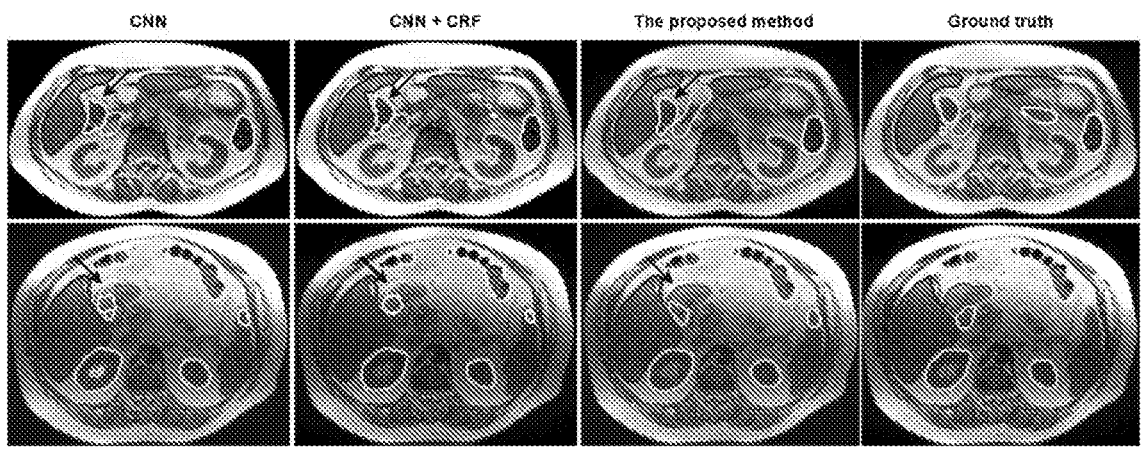
FIG. 6. Selected slices where small portion of bowel and stomach were mislabeled as kidney.
Figure 7:
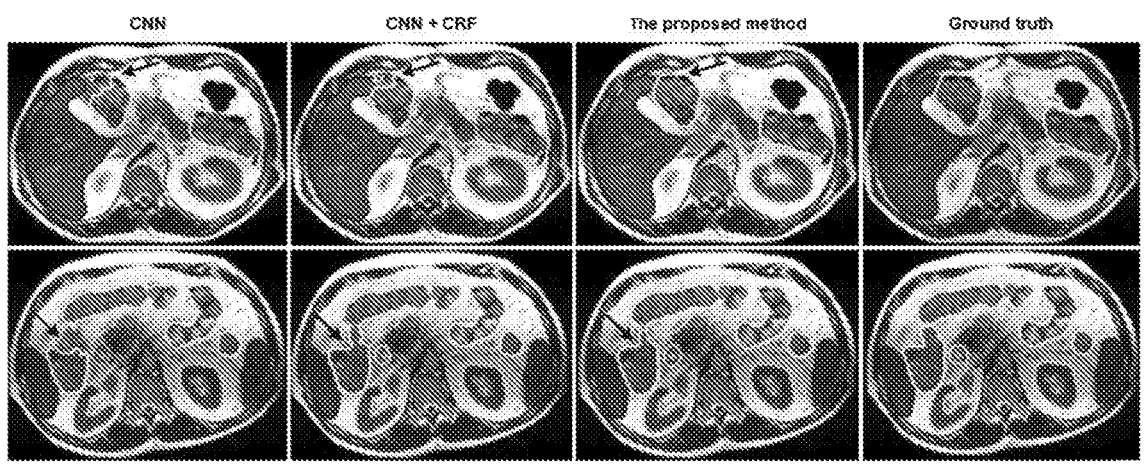
FIG. 7. Selected slices where small portion of bowel was mislabeled as stomach.

The segmentation results of selected slices are demonstrated in FIG. 6 and FIG. 7. FIG. 6 shows slices where small portions of stomach and bowel were misclassified as kidney (indicated by the black arrow in FIG. 6). FIG. 7 shows a similar situation where part of the bowel was mislabeled as stomach. This is because stomach and bowel share similar textural information because both were filled with chyme. As a result, the stomach may sometimes show up at improper locations such as the right side of the upper abdomen (indicated by black arrow in FIG. 7). Anatomically, kidneys are almost always posterior to the bowel and stomach and stomach should be on the left side of the upper abdomen. However, voxels were classified independent to each other in CNN. Misclassified organs may appear at unreasonable locations and result in anatomically implausible segmentation. Post-processing CRF could sometimes fix the errors when the erroneous labeling was small as shown in the top row in FIG. 6. However, it may fail when the erroneous labeling was large as shown in the bottom row in FIG. 6 and FIG. 7 due to its limited ability in modeling the complex global structural context. On the contrary, the same problems did not occur when the erroneous labels of sub-CNN1 were iteratively fixed using follow up correction networks.

DICE Coefficients and Hausdorff Distances

The average Dice coefficients were calculated and reported in TABLE 1 for the 10 testing datasets. The CNN+CRF method could remove some of the spurious labels and make the results more plausible than the CNN. However, it may sometimes remove true positive labels while removing the false positive ones resulting in decreased Dice. The Dice of duodenum is the lowest among the segmented target organs. It was challenging to contour duodenum even manually because duodenum is a relatively small structure, which often has highly unstable shapes and blurred boundaries. The beginning (the interface of duodenum and stomach) and the end (the interface of duodenum and jejunum) of the duodenum were not well controlled in manual contouring. Therefore, there are sometimes large discrepancies between the automatic and manual contouring results at both ends. The Dice drops significantly after CRF for duodenum because the label of duodenum often appears as small isolated segments, which are treated as erroneous labels in the CRF post-processing. On the contrary, the Dice increases for all the organs after the correction network.

TABLE 1

DICE comparison for CNN, CNN + CRF and the disclosed method on the 10 testing cases, mean (standard deviation). Bold values are the best values (highest DICE mean values and lowest DICE standard deviations)

| | DICE | | | | |
|---|---|---|---|---|---|
| | Liver | Kidney | Stomach | Bowel | Duodenum |
| CNN | 94.7 (0.89) | 92.0 (2.49) | 80.7 (5.57) | 84.2 (2.23) | 60.4 (7.06) |
| CNN + CRF | 94.4 (0.88) | 93.5 (1.51) | 82.1 (5.81) | 83.9 (2.71) | 39.3 (19.75) |
| CNN + Correction Network | 95.3 (0.73) | 93.1 (2.22) | 85.0 (3.75) | 86.6 (2.69) | 65.5 (8.90) |

Hausdorff Distances (HD) were computed to measure the mean and maximum distance differences between the surfaces of the predicted segmentation volume and the ground truth volume. To do so, surfaces of the predicted segmentation volume and the ground truth volume were densely meshed into triangular elements and HD values were calculated using the Euclidean distances between the nearest vertices from the two meshing surfaces. The relative large HD values for the CNN were mainly due to the erroneous labels such as the ones shown in FIG. 6 and FIG. 7. Compared to CNN+CRF, the CNN+Correction Network was able to further improve the results as evidenced by the reduced HD values in TABLE 2.

TABLE 2

HD comparison for CNN, CNN + CRF and the disclosed method on the 10 testing cases, mean (standard deviation) [maximum] in mm. Bold values are the best values (lowest HD values).

| | Hausdorff distance | | | | |
|---|---|---|---|---|---|
| | Liver | Kidney | Stomach | Bowel | Duodenum |
| CNN | 5.72 (3.70) [45.5] | 6.79 (6.46) [43.6] | 8.59 (9.15) [63.0] | 6.57 (6.26) [57.3] | 8.84 (8.46) [48.1] |
| CNN + CRF | 5.65 (2.57) [23.7] | 6.29 (5.10) [35.6] | 7.51 (5.68) [40.3] | 6.58 (6.04) [54.8] | 16.65 (14.83) [61.5] |
| CNN + Correction Network | 5.41 (2.34) [22.1] | 6.23 (4.59) [25.1] | 6.88 (4.89) [35.4] | 5.90 (4.05) [38.4] | 7.99 (6.84) [39.8] |

Test on Kidney Transplanted Patient

Figure 8:
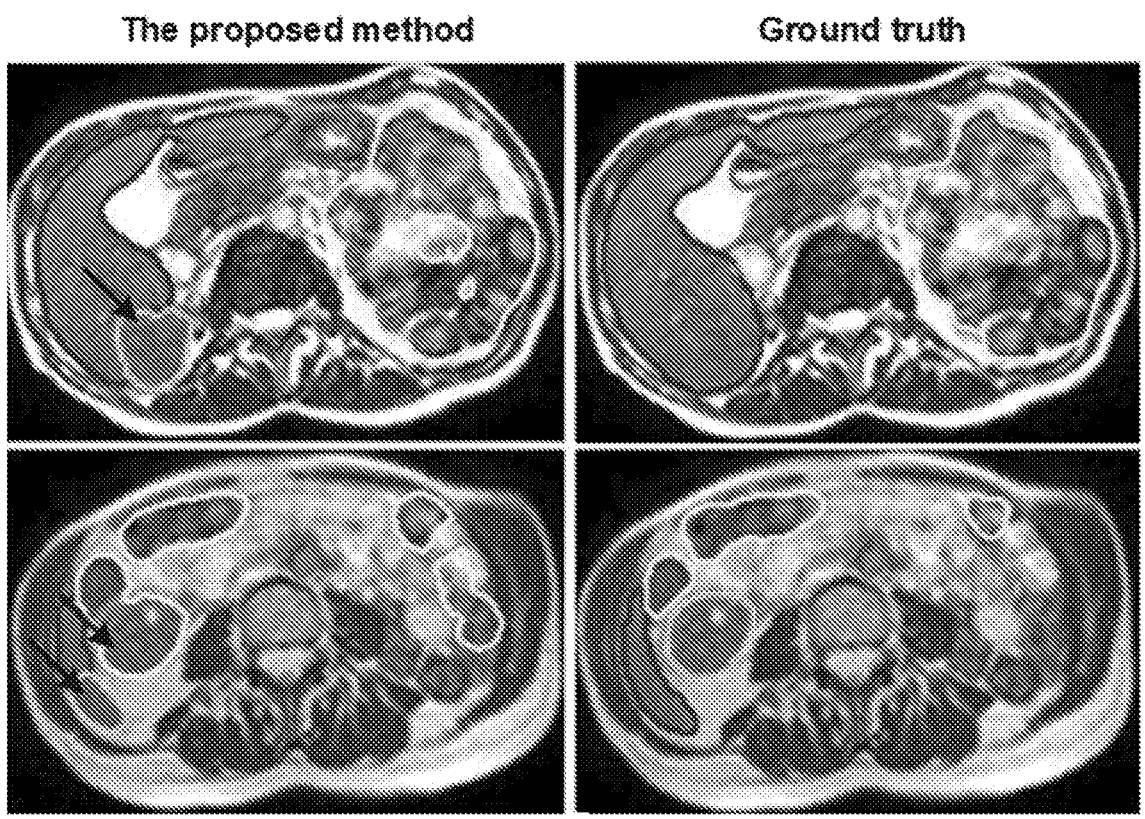
FIG. 8. The segmented kidney shows up at its normal location as opposed to the transplanted location, suggesting the network's ability to enforce anatomical constraints.

The disclosed method was tested on a patient with a transplanted kidney. The patient has only one transplanted kidney at location more anterior than normal kidney location. Because the network implicitly learns and enforces the relative location of the organs, the segmented kidney still shows up at its normal location as indicated by the black arrow in FIG. 8. The transplanted kidney was misclassified as part of bowel since the kidney was at a location usually occupied by bowel. This implies that the network was not applicable to patients with transplanted organs that would normally appear at different from normal locations. It was attempted to train the network on a patch-based manner where image patches were randomly sampled and fed into the network. In this situation, the network generated inferior results in correcting erroneous labels suggesting its impaired ability in modeling the global anatomical constraints. Therefore, it is important to train the network using the whole image so that the anatomical contextual information is learned.

Time Cost Analysis

The disclosed network took ~12 h to train on the 100 patient datasets. With an image size of 128×128×64 pixels, the contour prediction of these organs took ~5 s per patient. A contouring experiment was performed to examine the potential clinical utility of the disclosed method. Three medical physicist residents participated in the experiment to contour the organs with and without the help of the initial contours that were predicted by the disclosed method. The dataset was contoured using an in-house contouring software. The setup time prior to the actual contouring such as file transfer was not considered as part of the actual contouring time cost. For comparison, the time costs of the manual contouring process were recorded. Instead of absolute time cost, relative time cost ratios were reported to eliminate the time cost variability in different participants. The results are reported in TABLE 3. With the help of the initial contours, the manual contouring was on average about 4 times faster than before.

TABLE 3

The time cost was reported as the ratio of time spent on correcting the auto-segmented contours over the time spent on contouring the organs from scratch

| Participant 1 | Participant 2 | Participant 3 | Mean |
| --- | --- | --- | --- |
| 0.19 | 0.26 | 0.30 | 0.25 |

DISCUSSION

It is very challenging to automatically segment the digestive organs because the sizes, shapes, and appearances of the digestive organs change largely from day to day depending on food intake and metabolic processes. Traditional image segmentation methods that use hand crafted features have had very limited success in application to the gastrointestinal tract. CNN-based segmentation methods have shown the state-of-art performance in many image processing tasks. One limitation of the CNN methods is that the networks classify each voxel independently and may result in unreasonable segmentation. This phenomenon is more evident in segmenting digestive organs, which share similar appearance textures. To generate reasonable labels, a correction network was used to iteratively fix the erroneous labels and improve the segmentation accuracy. By comparison, the disclosed correction network has shown superior performance to the DC-CRF. Unlike the CRF which is an add-on post-processing step after the CNN, the correction network could be effectively included in the network and trained from end-to-end using piecewise training.

In the design of the correction network, it was attempted to keep only one sub-CNN and iterate over the same sub-CNN for multiple times while fixing the results from sub-CNN1. This is equivalent to use a recurrent network design for the correction network. However, the results were inferior to the current network design. This suggests that it is advantageous to use multiple dedicated sub-networks to improve the result from their immediate previous networks. This could be due to the relatively stable label distribution of the output of a certain sub-CNN at a certain stage of the network. This could also justify the choice of independent piecewise training of the dedicated parameters of each sub-CNNs in the correction network. After experimenting with multiple numbers of sub-CNNs in the correction network, it was found out that the performance almost stabilized after two sub-CNNs. Therefore, an empirical of two sub-CNNs were used in the design of current correction network.

In addition to the model reported here, several patient-specific models were also trained. For a patient-specific model, datasets of 15 fractions of single patient were applied. The first 10 fractions were used for training and the rest five fractions were used for testing. The training datasets and the testing datasets of a patient-specific model shared similar image features since they were from the same patient. It was expected that such patient-specific models would outperform the generic model that was trained using the datasets of the 100 different patients. Surprisingly, the patient-specific model and the generic model had roughly the same performance. This could be due to a smaller number of training datasets (10 fractions) used for the patient-specific model.

For the datasets used in this study, all patients were setup consistently in the same pose during treatment. Rotation or flipping of the training images is undesired in this case since the rotation or flipping may deteriorate the to-be-learned global anatomical constraints. Additional post-processing procedures were not used to refine the segmentation results of the correction network.

Apart from its clinical usage, the disclosed method could also be used to pre-segment the 3D MRIs prior to manual correction for training datasets preparation. This could greatly expedite the process of manual contouring and potentially alleviate the commonly faced problem of shortage of training datasets in medical image deep-learning research.

CONCLUSION

A novel network was developed to segment liver, kidneys, stomach, bowel, and duodenum in 3D ViewRay MRIs. This network can be useful to expedite the manual OAR contouring in MR-IGART.

What is claimed is:

1. A method of segmenting contours of one or more abdominal cavity organs comprising:
(i) providing an image dataset;
(ii) applying a first convolutional neural network (sub-CNN1) to the image dataset, resulting in a label probability map of sub-CNN1 ($P_1$) (segmentation results);
(iii) applying a correction network comprising a second convolutional neural network (sub-CNN2) and a third convolutional neural network (sub-CNN3) to $P_1$ comprising:
(a) applying the second convolutional neural network (sub-CNN2) to the label probability map of sub-CNN1 ($P_1$), resulting in a label probability map of sub-CNN2 ($P_2$);
(b) concatenating the image datasets, $P_1$, and $P_2$; and
(c) applying the third convolutional neural network (sub-CNN3) to the image datasets, $P_1$ and $P_2$;
wherein applying the first convolutional neural network and the correction network results in accurately segmented organs in images; and (iv) training sub-CNN1, sub-CNN2, and sub-CNN3, wherein training comprises:
    training each of sub-CNN1, sub-CNN2, and sub-CNN3 parameters using whole 3D images to incorporate anatomical contextual information;
    randomizing sub-CNN1, sub-CNN2, and sub-CNN3 parameters using a Gaussian distribution;
    calculating a cross entropy loss function using a softmax classifier for sub-CNN1, wherein sub-CNN2 and sub-CNN3 are constant;
    calculating a cross entropy loss function using a softmax classifier for sub-CNN2, wherein sub-CNN1 and sub-CNN3 are constant; and
    calculating a cross entropy loss function using a softmax classifier for sub-CNN3, wherein sub-CNN1 and sub-CNN2 are constant.

2. The method of claim 1, wherein one or more abdominal cavity organs are selected from gastrointestinal (GI) organs or organs at risk (OAR).

3. The method of claim 1, wherein the one or more abdominal cavity organs are selected from one or both kidneys, a liver, a stomach, a bowel, or a duodenum.

4. The method of any one of claim 1, wherein the one or more abdominal cavity organs is an unstable organ selected from one or more of the group consisting of: a stomach, a bowel, and a duodenum.

5. The method of claim 1, wherein the label probability map of sub-CNN1 ($P_1$) (segmentation results) are refined through iterative error feedback comprising feeding erroneous labeling and the image dataset into the correction network, wherein the correction network iteratively corrects erroneous labels and improves segmentation accuracy.

6. The method of claim 1, wherein the image dataset is a MR image dataset or a CT image dataset.

7. The method of claim 1, wherein the correction network:
    generates segmentations with possible organs shapes and locations;
    iteratively improves the $P_1$ (the segmentation results);
    is incorporated into the whole network and capable of being trained from end-to-end; and
    performs robustly and does not require careful parameter fine tuning.

8. The method of claim 1, wherein the correction network implicitly enforces anatomical constraints selected from the group consisting of: (i) a shape of one or more organs or (ii) relative locations of multiple organs.

9. An MRI-guided radiation treatment system comprising the use of the method of claim 1.

* * * * *